US009168562B2

(12) United States Patent
Gilchrist

(10) Patent No.: US 9,168,562 B2
(45) Date of Patent: Oct. 27, 2015

(54) SYRINGE-ASSIST DEVICE AND METHOD FOR UTILIZING THE SAME

(71) Applicant: Ann M. Gilchrist, Kalamazoo, MI (US)

(72) Inventor: Ann M. Gilchrist, Kalamazoo, MI (US)

(73) Assignee: Ann Gilchrist, Kalamazoo, MI (US)

( * ) Notice: Subject to any disclaimer, the term of this patent is extended or adjusted under 35 U.S.C. 154(b) by 148 days.

(21) Appl. No.: 14/051,001

(22) Filed: Oct. 10, 2013

(65) Prior Publication Data

US 2015/0105733 A1 Apr. 16, 2015

(51) Int. Cl.

*A61M 5/315* (2006.01)
*B05C 17/01* (2006.01)
*A61M 5/142* (2006.01)
*B65D 83/00* (2006.01)

(52) U.S. Cl.

CPC ................ *B05C 17/01* (2013.01); *A61M 5/142* (2013.01); *B65D 83/0005* (2013.01)

(58) Field of Classification Search

CPC .... A47K 5/1202; F16N 3/12; B65D 83/0005; A61M 5/142; A61M 5/148; A61M 5/2033; A61M 2005/2013; B05C 17/01
USPC .......... 222/325, 326, 327; 604/131, 134, 135, 604/136, 137, 241, 218
See application file for complete search history.

(56) References Cited

U.S. PATENT DOCUMENTS 1,718,596 A 6/1929 Smith
1,838,039 A * 12/1931 Montuori ...................... 604/220
2,472,116 A * 6/1949 Maynes ........................ 604/136
2,491,978 A 12/1949 Helfman et al.
2,664,086 A * 12/1953 Transue ........................ 604/157
2,892,457 A 6/1959 Sturtz
3,493,503 A * 2/1970 Morris .......................... 210/778
3,797,487 A * 3/1974 Schmidt ........................ 604/232
3,880,163 A 4/1975 Ritterskamp
3,882,863 A * 5/1975 Sarnoff et al. ................ 604/136
4,014,797 A * 3/1977 Raines et al. ................ 210/446
4,067,334 A 1/1978 Haller
4,132,231 A 1/1979 Puccio
4,231,368 A 11/1980 Becker
4,407,283 A * 10/1983 Reynolds ...................... 604/136
4,465,478 A 8/1984 Sabelman et al.
4,601,711 A 7/1986 Ashbury et al.
5,176,646 A 1/1993 Kuroda
5,320,609 A * 6/1994 Haber et al. .................. 604/135

(Continued)

FOREIGN PATENT DOCUMENTS

JP 2000202024 A 7/2000

*Primary Examiner* — J. Casimer Jacyna
(74) *Attorney, Agent, or Firm* — Honigman Miller Schwartz and Cohn LLP; Douglas H. Siegel; Jonathan P. O'Brien

(57) ABSTRACT

A syringe-assist device including a housing portion, an actuator portion, and a syringe-supporting member. The housing portion includes body defining an axial passage. The actuator portion is connected to and is partially disposed within the axial passage of the body. The syringe-supporting member is movably-disposed within the axial passage. The syringe-supporting member fluidly separates the axial passage into a first, proximal passage portion and a second, distal passage portion. The actuator portion is movably-disposed within the second, distal passage portion of the axial passage. The syringe-supporting member defines a fluid-flow passage that fluidly-connects the first, proximal passage portion of the axial passage to the second, distal passage portion of the axial passage. A method is also disclosed.

22 Claims, 11 Drawing Sheets

(56) References Cited

U.S. PATENT DOCUMENTS

| | | | | |
|---|---|---|---|---|
| 5,501,670 | A * | 3/1996 | Sak | 604/110 |
| 5,545,140 | A | 8/1996 | Conero et al. | |
| 5,599,315 | A | 2/1997 | McPhee | |
| 5,722,956 | A | 3/1998 | Sims et al. | |
| 5,800,405 | A | 9/1998 | McPhee | |
| 5,954,695 | A | 9/1999 | Sims et al. | |
| 6,544,233 | B1 * | 4/2003 | Fukui et al. | 604/191 |
| 7,578,212 | B2 | 8/2009 | Kleyman et al. | |
| 7,867,197 | B2 | 1/2011 | Sims et al. | |
| 8,231,576 | B2 | 7/2012 | Sims et al. | |
| 2009/0137965 | A1 | 5/2009 | Kim et al. | |

* cited by examiner

SYRINGE-ASSIST DEVICE AND METHOD FOR UTILIZING THE SAME

FIELD OF THE INVENTION

The disclosure relates to a syringe-assist device and a method for utilizing the same.

DESCRIPTION OF THE RELATED ART

Syringes are known in the art. The present invention overcomes drawbacks associated with the operation of a syringe by setting forth a device and methodology for utilizing the same that assists in the operation of a syringe.

BRIEF DESCRIPTION OF THE DRAWINGS

The disclosure will now be described, by way of example, with reference to the accompanying drawings, in which.

SUMMARY

Figure 1:
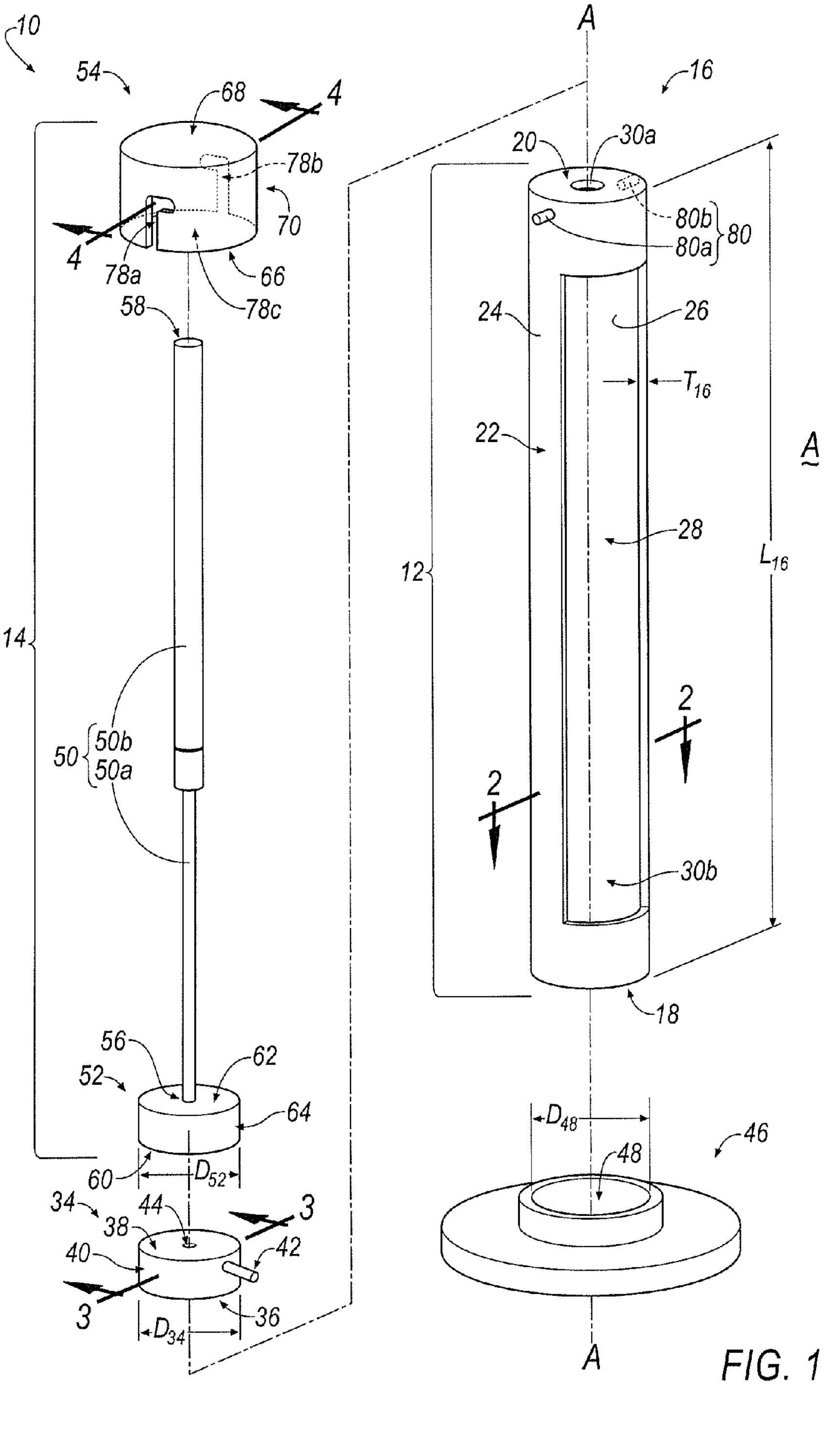
FIG. 1 is an exploded view of an exemplary syringe-assist device in accordance with an exemplary embodiment of the invention.

One aspect of the disclosure provides a syringe-assist device including a housing portion, an actuator portion and a syringe-supporting member. The housing portion includes a body that defines an axial passage. The actuator portion is connected to and is partially disposed within the axial passage of the body. The syringe-supporting member is movably-disposed within the axial passage. The syringe-supporting member fluidly separates the axial passage into a first, proximal passage portion and a second, distal passage portion. The actuator portion is movably-disposed within the second, distal passage portion of the axial passage. The syringe-supporting member defines a fluid-flow passage that fluidly-connects the first, proximal passage portion of the axial passage to the second, distal passage portion of the axial passage.

In some examples, a container is removably-disposed within the first, proximal passage portion of the axial passage, and, a syringe is removably-disposed within the second, distal passage portion of the axial passage. The syringe is in fluid communication with a distal opening of the fluid-flow passage, and, the container is in fluid communication with a proximal opening of the fluid-flow passage such that a fluid contained within the syringe is transferable from the syringe through the fluid-flow passage and into the container.

In some implementations, the body is a tube-shaped body having a proximal end portion, a distal end portion and a side portion extending between the proximal end portion and the distal end portion. Each of the proximal end portion, the distal end portion and the side portion are defined by an outer surface and an inner surface such that the tube-shaped body is defined by a thickness extending between the outer surface and the inner surface.

In some instances, the inner surface defines the axial passage. The axial passage extends through the tube-shaped body along a central axis between the proximal end portion and the distal end portion of the tube-shaped body. The inner surface defines the axial passage to form an axial passage diameter. The outer surface defines the tube-shaped body to form a body diameter.

In some examples, the tube-shaped body forms a first opening and a second opening each extending through a thickness of the tube-shaped body. The first opening and the second opening permit the axial passage to be in fluid communication with surrounding atmosphere.

The first opening is formed by the distal end portion of the tube-shaped body and is axially-aligned with the central axis. The second opening is formed by the side portion of the tube-shaped body and extends along most of a length of the tube-shaped body. The second opening is approximately equal to but slightly greater than half of a circumference of the tube-shaped body.

In some implementations, the syringe-supporting member includes a handle extending from an outer side surface of the syringe-supporting member.

In some instances, the syringe-supporting member includes a diameter that is approximately equal to but slightly less than an axial passage diameter formed by the axial passage of the tube-shaped body.

In some examples, the syringe-assist device further includes a base member connected to a proximal end portion of the housing portion.

In some implementations, the actuator portion includes: an actuator having a proximal end and a distal end, a head member connected to the proximal end of the actuator, and a cap member connected to the distal end of the actuator.

In some instances, a first portion of the actuator and the head member are movably-disposed within the second, distal passage portion of the axial passage. A second portion of the actuator and the cap member are arranged exterior of the housing portion and not within the axial passage.

In some examples, the actuator is a gas damper including a piston rod that is connected to and movably-disposed within a cylinder containing a gas.

In some implementations, the head member includes a diameter that is approximately equal to but slightly less than a diameter of the axial passage of the body of the housing portion.

In some instances, the cap member includes a proximal end surface, an outer distal end surface, an outer side surface, an inner side surface and an inner distal end surface. The inner side surface and the inner distal end surface define the cap member to include a recess. The inner side surface defines the cap member to include an inner diameter that is approximately equal to but slightly greater than a body diameter defined by an outer surface of the body of the housing portion.

In some examples, the cap member includes a thickness extending between the outer side surface and the inner side surface. The cap member forms a first opening and a second opening arranged in a diametrically-opposing relationship.

In some implementations, each of the first opening and the second opening include an L-shaped geometry.

In some instances, a first flange and a second flange are arranged proximate a distal end portion of the body of the housing. The cap member is selectively-arranged upon the distal end portion of the body of the housing such that when the first flange and the second flange are respectively-arranged within the first opening and the second opening the cap member is selectively-coupled to the distal end portion of the body of the housing.

Another aspect of the disclosure provides a method including the steps of: providing a syringe-assist device including a housing portion having a body that defines an axial passage and an actuator portion partially disposed within the axial passage of the body; movably-disposing a syringe-supporting member within the axial passage for fluidly-separating the axial passage into a first, proximal passage portion and a second, distal passage portion; movably-disposing the actuator portion within the second, distal passage portion of the axial passage, the syringe-supporting member defines a fluid-flow passage that fluidly-connects the first, proximal passage portion of the axial passage to the second, distal passage portion of the axial passage; removably-disposing a container within the first, proximal passage portion of the axial passage such that the container is in fluid communication with a proximal opening of the fluid-flow passage; removably-disposing a syringe within the second, distal passage portion of the axial passage such that the syringe is in fluid communication with a distal opening of the fluid-flow passage; and actuating the actuator portion for discharging a fluid contained within the syringe through the fluid-flow passage and into the container.

In some examples, the removably-disposing the container step includes: arranging a lower, proximal end surface of the container adjacent the proximal end portion of the tube-shaped body; and, after the arranging step, the method further comprises the step of: arranging the proximal end surface of the syringe-supporting member adjacent an upper, distal end surface of the container.

In some implementations, the removably-disposing the syringe step includes: disposing a distal tip of a wheel filter attached to a proximal end of the syringe in the fluid-flow passage of the syringe-supporting member.

In some instances, the actuating the actuator portion step includes: applying a pushing force to a distal end of the actuator portion.

In some examples, the actuator portion includes a gas damper actuator including a piston rod movably-disposed within a cylinder. The applied pushing force results in the steps of: engaging the piston rod with a plunger of the syringe; and retracting the piston rod into the cylinder.

In some implementations, after the retracting step, the method further includes the steps of: twisting the distal end of the actuator portion for locking the distal end of the actuator portion to a distal end portion of the body of the housing; and extending the piston rod from the cylinder and toward the plunger of the syringe for discharging the fluid contained within the syringe through the fluid-flow passage and into the container.

DETAILED DESCRIPTION OF THE INVENTION

The Figures illustrate exemplary embodiments of a syringe-assist device and a method for utilizing the same. Based on the foregoing, it is to be generally understood that the nomenclature used herein is simply for convenience and the terms used to describe the invention should be given the broadest meaning by one of ordinary skill in the art.

Figure 6A:
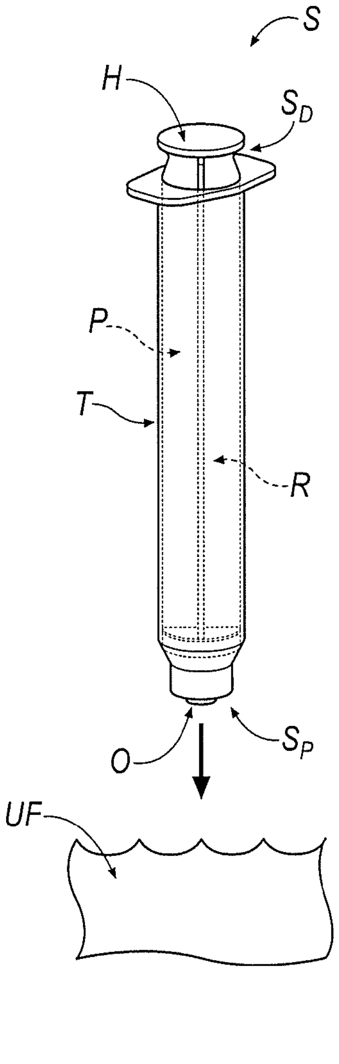
FIGS. 6A-6C are views of a method for operating a syringe.
Figure 6B:
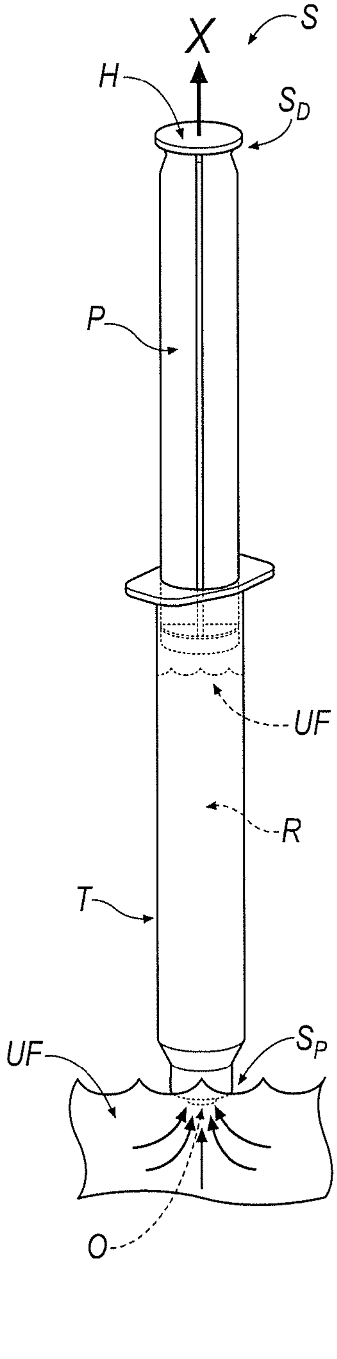
Figure 6C:
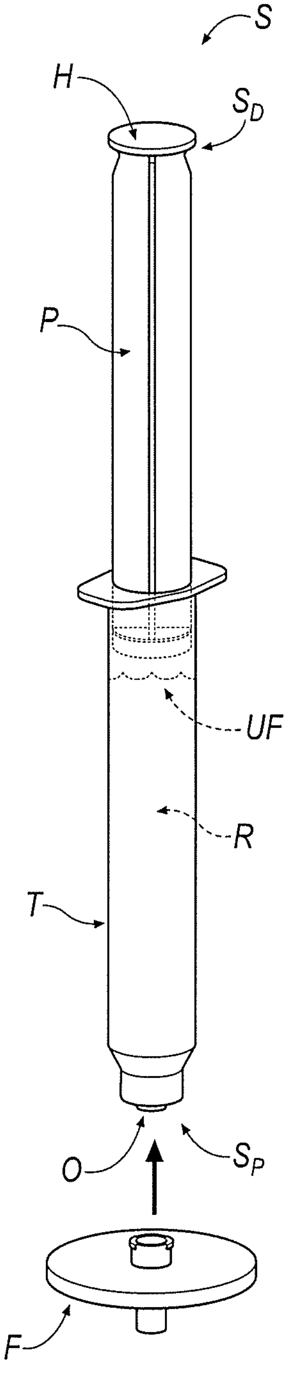
Figure 6D:
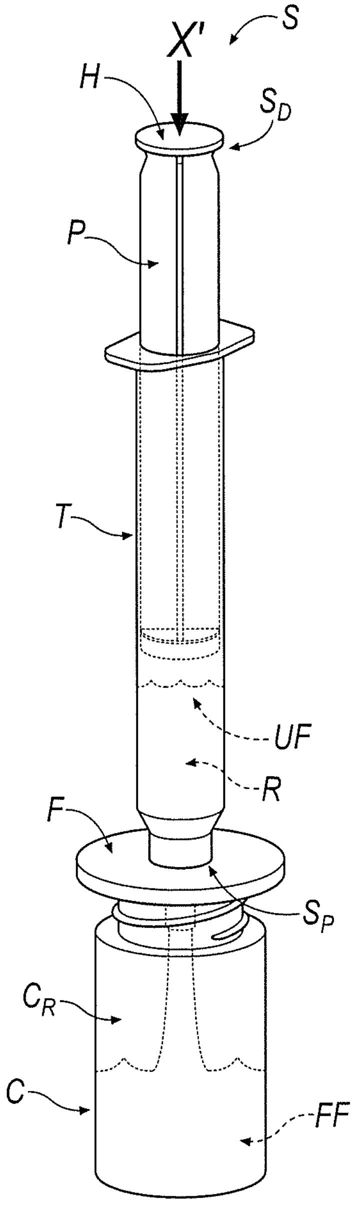
FIGS. 6D is a view of method for discharging a fluid from the syringe of FIG. 6C into a container.

Prior to describing embodiments of the invention, reference is made to FIGS. 6A-6D, which illustrates an exemplary syringe S. The syringe S includes a tube-shaped member T and a plunger P that is slidably-disposed in an unfiltered fluid reservoir R formed by the tube-shaped member T. A distal end $S_D$ of the syringe S is generally defined by a pushing head H of the plunger P. A proximal end $S_P$, of the syringe S is generally defined by a fluid aspirating/expelling opening O (see, e.g., FIGS. 6A-6C). As seen in FIGS. 6C-6D, a wheel filter F may be attached to the proximal end Sp of the syringe S in order to close-out the fluid aspirating/expelling opening, O.

As seen in FIGS. 6A-6B, the unfiltered fluid reservoir R may be loaded with unfiltered fluid UF by pulling the plunger P in a direction according to arrow X (see, e.g., FIG. 6B). Then, as the wheel filter F is attached to the proximal end Sp of the syringe S as seen in FIG. 6C, a plunger-actuating force (according to the direction of arrow X' as seen in, e.g., FIG. 6D) may be imparted to the pushing head H of the plunger P for evacuating the unfiltered fluid UF from the unfiltered fluid reservoir R and out of the proximal end Sp of the syringe S. Prior to being evacuated out of the proximal end Sp of the syringe S the unfiltered fluid UF passes through the wheel filter F in order to remove contaminates from the unfiltered fluid UF. Once the unfiltered fluid UF passes through the wheel filter F the unfiltered fluid UF may be referred to as filtered fluid FF (as seen in, e.g., FIG. 6D); the filtered fluid FF may be deposited into a filtered fluid container C (as seen in, e.g., FIG. 6D).

Referring to FIGS. 1 and 5A-5G, an exemplary syringe-assist device is shown generally at 10. As seen in FIG. 1, the syringe-assist device 10 generally includes a housing portion 12 and an actuator portion 14.

Figure 5A:
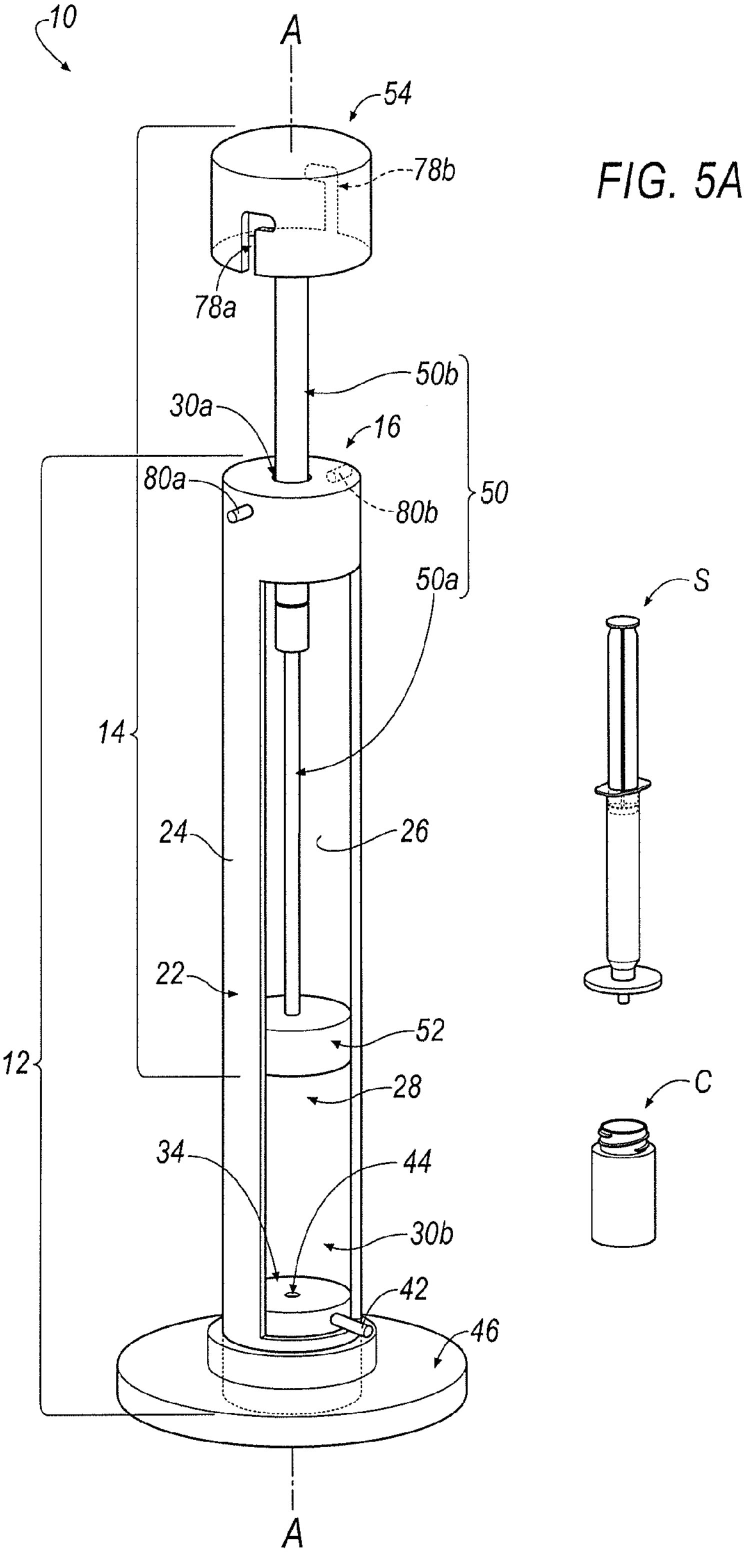
FIGS. 5A-5G are views of an exemplary method for utilizing the syringe-assist device of FIG. 1.
Figure 5B:
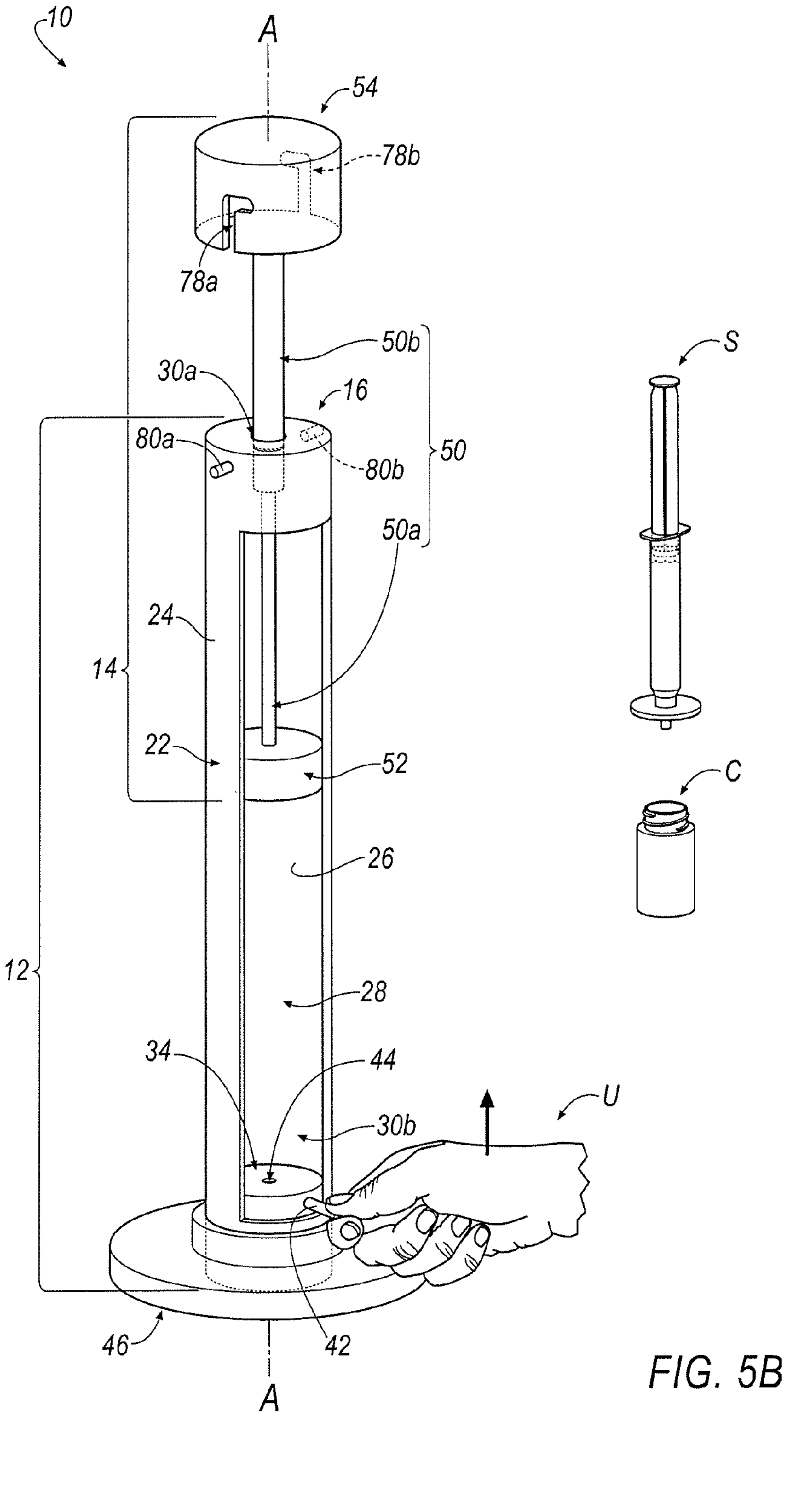
Figure 5C:
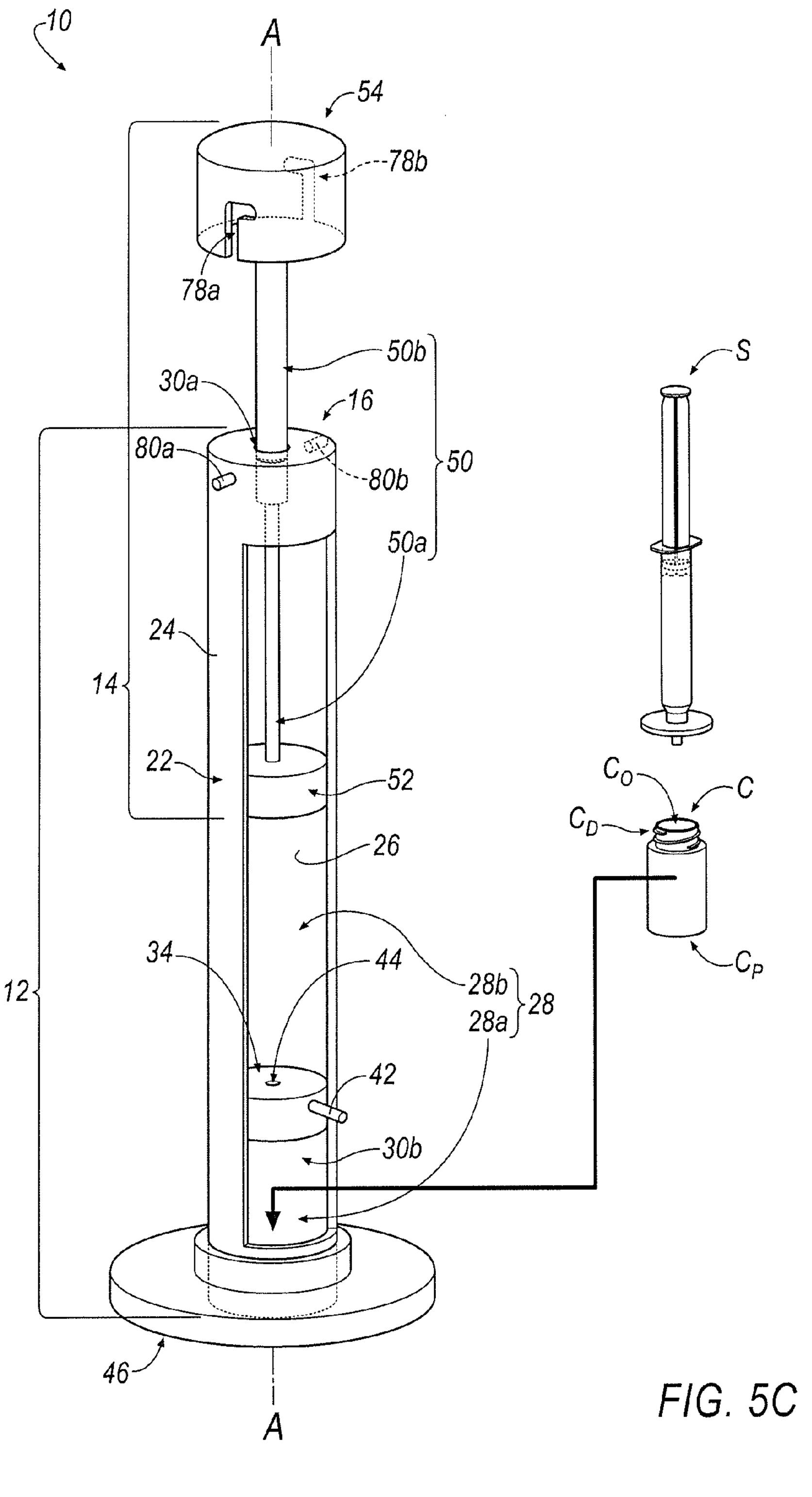
Figure 5D:
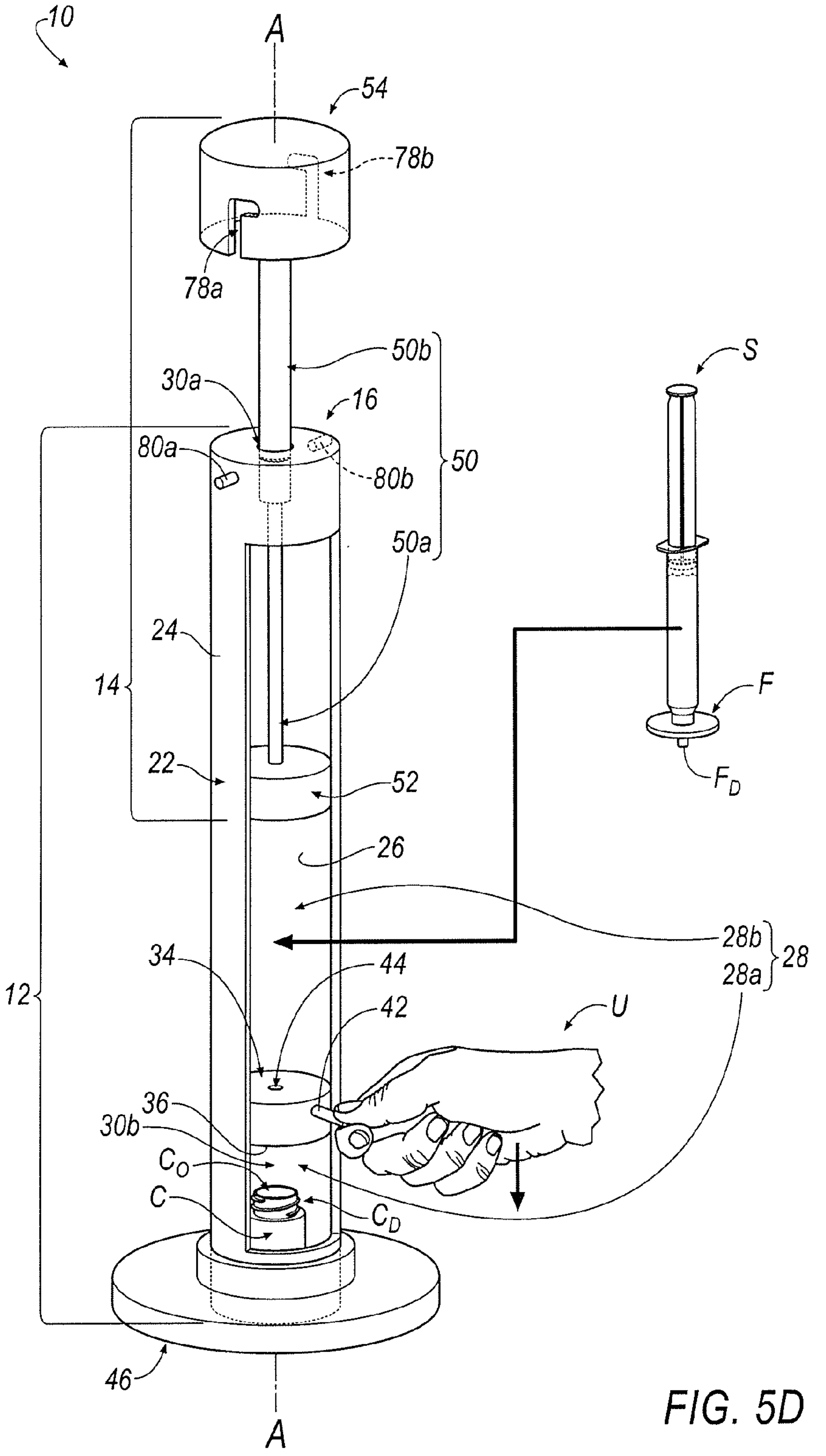
Figure 5E:
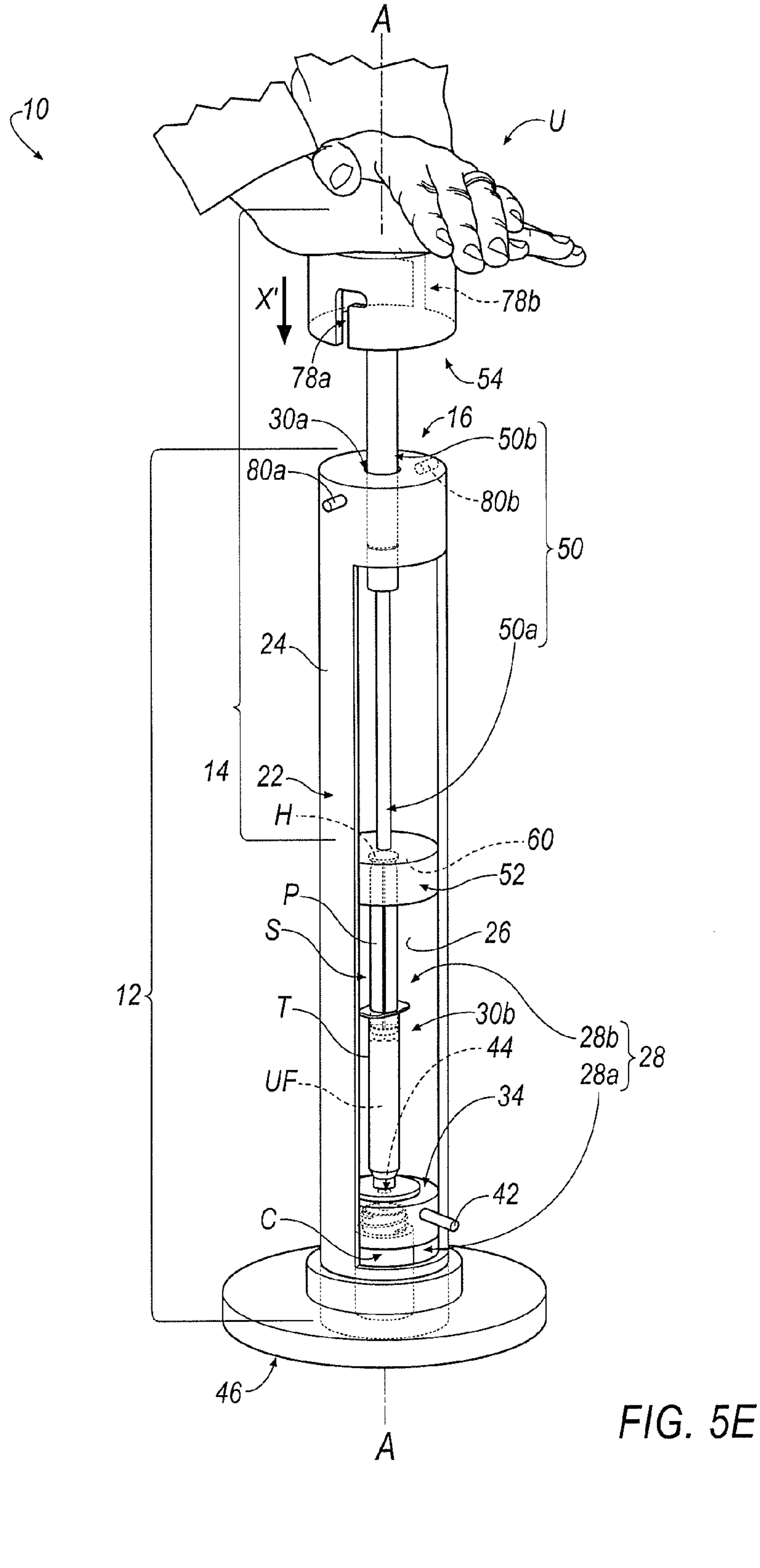
Figure 5F:
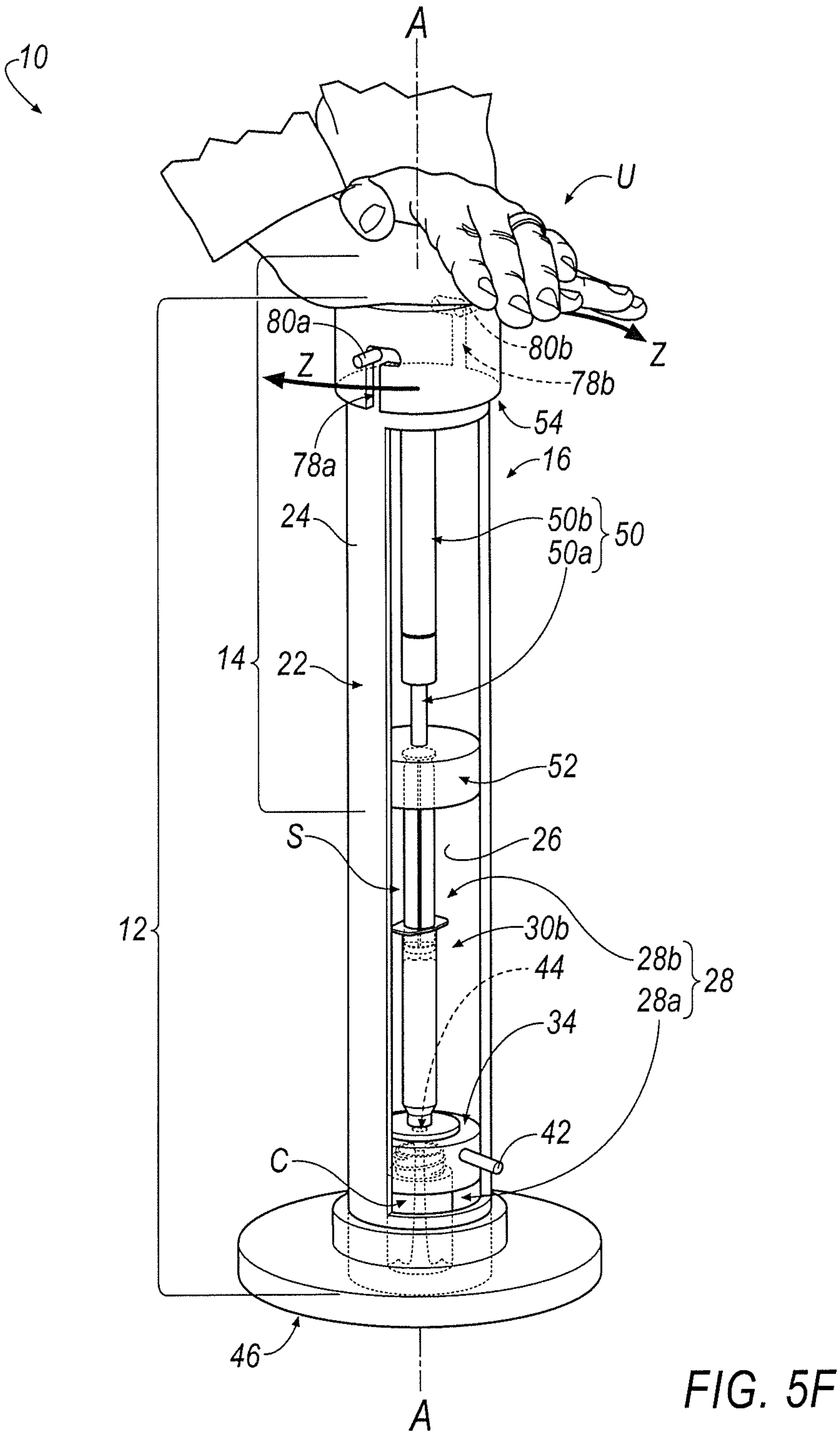

Referring to FIG. 5E, the housing portion 12 retains both the syringe S and the filtered fluid container C. Referring to FIGS. 5E-5F, a user U (see, e.g., FIGS. 5B and 5D-5G), imparts a push (see, e.g., FIG. 5E) and twist (see, e.g., FIG. 5F) to the actuator portion 14 in order to cause the actuator portion 14 to impart the plunger-actuating force X', as similarly described above in FIG. 6D, in order to evacuate the unfiltered fluid UF from the unfiltered fluid reservoir R of the syringe S and into the filtered fluid container C as filtered fluid FF.

Referring to FIG. 1, the housing 12 may be generally defined as a tube-shaped body 16 having a proximal end portion 18, a distal end portion 20 and a side portion 22 extending between the proximal end portion 18 and the distal end portion 20. Each of the proximal end portion 18, the distal end portion 20 and the side portion 22 may be defined by an outer surface 24 and an inner surface 26 such that the tube-shaped body 16 may be defined by a thickness $T_{16}$ extending between the outer surface 24 and the inner surface 26.

The inner surface 26 may define an axial passage 28 that extends through the tube-shaped body 16 along a central axis, A-A, between the proximal end portion 18 and the distal end portion 20 of the tube-shaped body 16. The inner surface 26 defines the axial passage 28 to form an axial passage diameter $D_{28}$ (see, e.g., FIG. 2). The outer surface 24 defines the tube-shaped body 16 to form a body diameter $D_{16}$ (see, e.g., FIG. 2).

The tube-shaped body 16 may form a first opening 30*a* (see, e.g., FIG. 1) and a second opening 30*b* (see, e.g., FIGS. 1-2) each extending through the thickness $T_{16}$ of the tube-shaped body 16. The first opening 30*a* and the second opening 30*b* permit the axial passage 28 to be in fluid communication with surrounding atmosphere, A.

The first opening 30*a* may be formed by the distal end portion 20 of the tube-shaped body 16. In some implementations, the first opening 30*a* may be axially-aligned with the central axis, A-A; as a result, the first opening 30*a* may alternatively be referred to as an axial opening.

Figure 2:
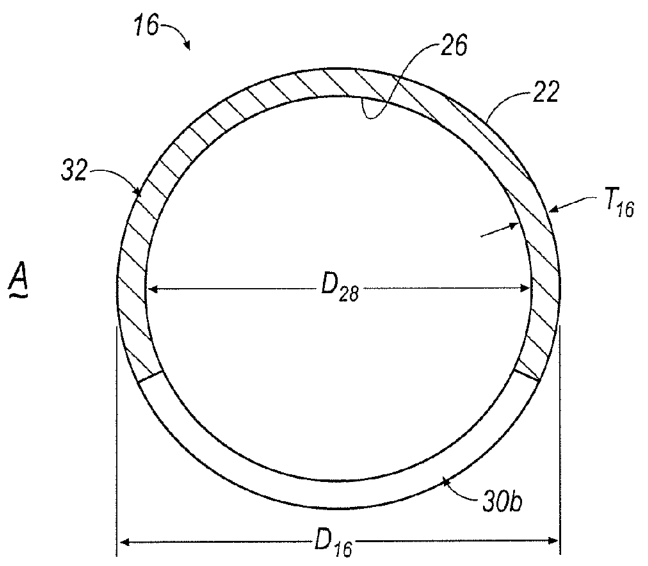
FIG. 2 is a cross-sectional view of the syringe-assist device according to line 2-2 of FIG. 1.

The second opening 30*b* may formed by the side portion 22 of the tube-shaped body 16. The second opening 30*b* may axially extend along most of a length $L_{16}$ (see, e.g., FIG. 1), of the tube-shaped body 16; in some implementations, the second opening 30*b* may axially extend along approximately about 50%, 60%, 75%, or 85% of the length, $L_{16}$, of the tube-shaped body 16. Referring to FIG. 2, the second opening 30*b* may be approximately equal to but slightly greater than half of a circumference 32 of the tube-shaped body 16.

Figure 3:
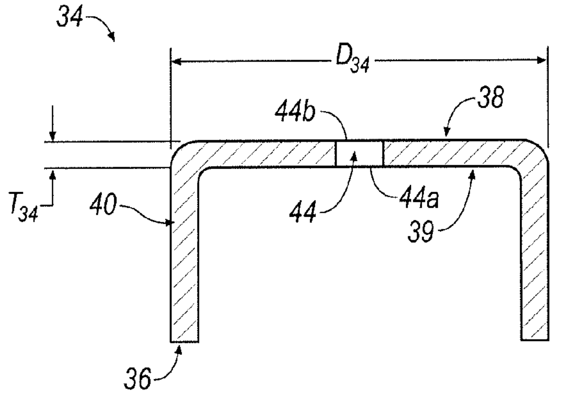
FIG. 3 is a cross-sectional view of the syringe-assist device according to line 3-3 of FIG. 1.

Referring to FIGS. 1 and 3, an exemplary syringe-supporting member is shown generally at 34. As seen in FIGS. 5A-5D, the syringe-supporting member 34 is slidably-arranged within the axial passage 28. As will be described in the following disclosure, the syringe-supporting member 34 fluidly separates the axial passage 28 into a first, proximal passage portion 28*a* and a second, distal passage portion 28*b*.

Referring to FIG. 1, the syringe-supporting member 34 may include a proximal end surface 36, an outer distal end surface 38 and an outer side surface 40. A handle 42 may be connected to and extend radially outwardly from the outer side surface 40 of the syringe-supporting member 34.

The outer side surface 40 defines the syringe-supporting member 34 to include a diameter, $D_{34}$ (see, e.g., FIG. 3). The diameter, $D_{34}$, of the syringe-supporting member 34 may be approximately equal to but slightly less than the axial passage diameter, $D_{28}$, of the axial passage 28 of the tube-shaped body 16.

Referring to FIGS. 1 and 3, the syringe-supporting member 34 may include a fluid-flow passage 44 that extends through a thickness $T_{34}$ of the syringe-supporting member 34. Referring to FIG. 3, the thickness $T_{34}$ of the syringe-supporting member 34 may be bound by the outer distal end surface 38 and an inner distal end surface 39. Access to the fluid-flow passage 44 is permitted by a first, proximal opening 44*a* formed by the inner distal end surface 39 of the syringe-supporting member 34 and a second, distal opening 44*b* formed by the outer distal end surface 38 of the syringe-supporting member 34. In some implementations, the fluid-flow passage 44 may be axially-aligned with the central axis, A-A; as a result, the fluid-flow passage 44 may alternatively be referred to as an axial fluid-flow passage. As will be described in the following disclosure, fluid-flow passage 44 of the syringe-supporting member 34 permits the first, proximal passage portion 28*a* of the axial passage 28 to be in fluid communication with the second, distal passage portion 28*b* of the axial passage 28 for permitting a fluid (e.g., the unfiltered fluid UF) contained within a syringe S that is arranged within the second, distal passage portion 28*b*, through the fluid-flow passage 44 and into a container, C, disposed within the first, proximal passage portion 28*a* (see, e.g., FIGS. 5C-5D).

Referring to FIG. 1, in some implementations, the housing 12 may be attached to a base member 46. The base member 46 may be defined by a substantially circular shape. The base member 46 may form a receiving opening or receiving pocket 48. The receiving pocket 48 may include a diameter, $D_{48}$, that is substantially equal to but slightly greater than a body diameter $D_{16}$ formed by the outer surface 24 of the tube-shaped body 16 such that the tube-shaped body 16 may be received by and frictionally-coupled to receiving pocket 48 of the base member 46.

Referring to FIG. 1, the actuator portion 14 may include an actuator 50, a head member 52 and a cap member 54. The actuator 50 includes a proximal end 56 and a distal end 58. The head member 52 is attached to the proximal end 56 of the actuator 50. The cap member 54 is attached to the distal end 58 of the actuator 50.

Figure 5G:
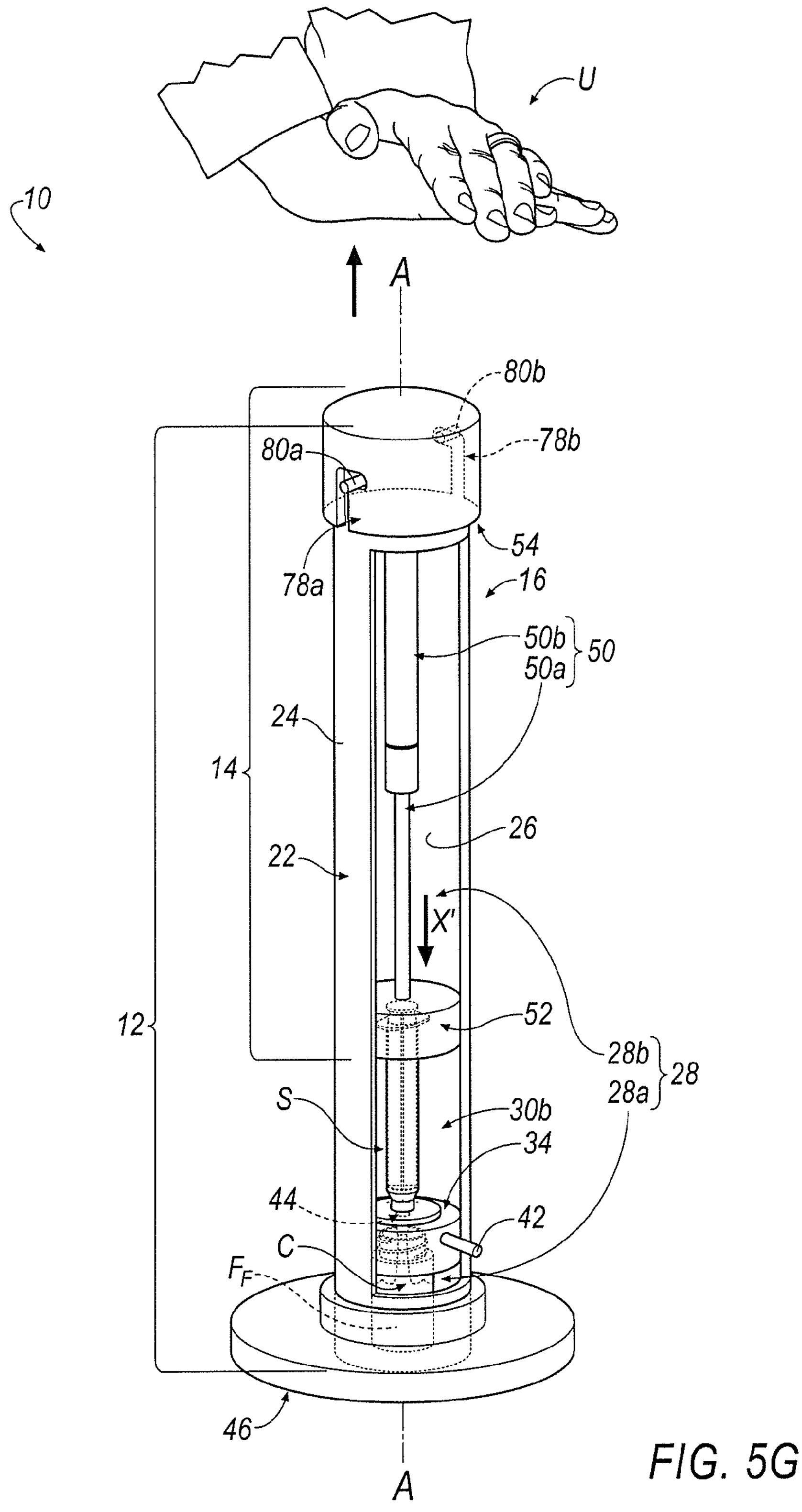

In some implementations, the actuator 50 may be a gas damper. The gas damper includes a piston rod 50*a* that is connected to and slidably-disposed within a cylinder 50*b*. A gas that is contained within the cylinder 50*b* biases the piston rod 50*a* in an extended state (see, e.g., FIGS. 1, 5A-5E, 5G); conversely, the piston rod 50*a* may be urged into/maintained within the cylinder 50*b* such that the piston rod 50*a* may be said to be arranged in a retracted state (see, e.g., FIG. 5F). Referring to FIG. 5F, when the piston rod 50*a* is arranged in the retracted state with respect to the cylinder 50*b*, the gas that is contained within the cylinder 50*b* may be compressed, thereby storing energy that may be utilized for returning the piston rod 50*a* back to the extended state with respect to the cylinder 50*b* as seen in FIG. 5G.

Referring to FIG. 1, the head member 52 may include a substantially similar geometry with respect to the syringe-supporting member 34 in that the head member 52 includes a proximal end surface 60, a distal end surface 62 and an outer side surface 64. The outer side surface 64 defines the head member 52 includes a diameter $D_{52}$. The diameter $D_{52}$ of the head member 52 may be approximately equal to but slightly less than the diameter $D_{28}$ of the axial passage 28 of the tube-shaped body 16. The proximal end 56 of the actuator 50 is attached to the distal end surface 62 of the head member 52.

Figure 4:
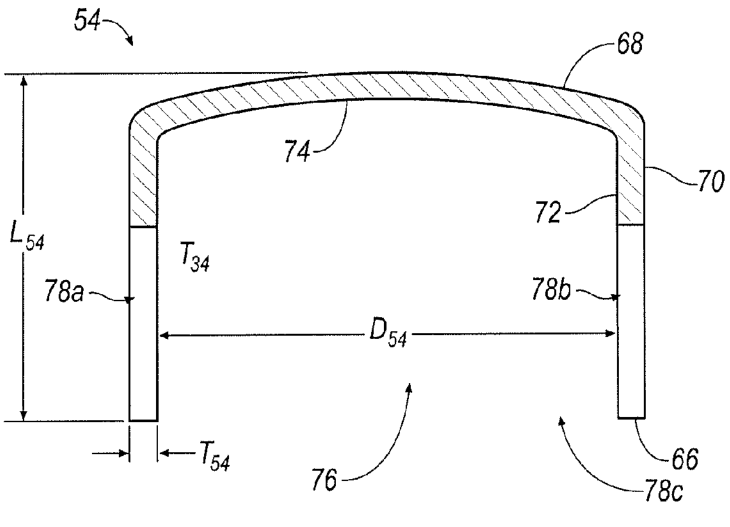
FIG. 4 is a cross-sectional view of the syringe-assist device according to line 4-4 of FIG. 1.

The cap member 54 includes a proximal end surface 66, an outer distal end surface 68, an outer side surface 70, an inner side surface 72 (see, e.g., FIG. 4) and an inner distal end surface 74 (see, e.g., FIG. 4). Referring to FIG. 4, the inner side surface 72 and the inner distal end surface 74 define the cap member 54 to include a recess 76. The distal end 58 of the actuator 50 is attached to the inner distal end surface 74 of the cap member 54.

Referring to FIG. 4, the inner side surface 72 defines the cap member 54 to include an inner diameter $D_{54}$. The inner diameter $D_{54}$ of the cap member 54 may be approximately equal to but slightly greater than the body diameter $D_{16}$ defined by the outer surface 24 of the tube-shaped body 16.

Referring to FIG. 4, the outer side surface 70 and the inner side surface 72 define the cap member 54 to include a thickness, $T_{54}$. The thickness, $T_{54}$, extends between the outer side surface 70 and the inner side surface 72.

Referring to FIGS. 1 and 4, the cap member 54 may further include at least one opening 78*a*, 78*b*, 78*c*. Some implementations of the invention include a first opening 78*a*, a second opening 78*b* and a third opening 78*c*. In an example, the first and second openings 78*a*, 78*b* each extend through the thickness, $T_{54}$, of the cap member 54. In an example, the first and second openings 78*a*, 78*b* of the cap member 54 are arranged in a diametrically-opposing relationship.

The first and second openings 78*a*, 78*b* may axially extend along most of a length $L_{54}$ (see, e.g., FIG. 4) of the cap member 54; in some implementations, the first and second openings 78*a*, 78*b* may axially extend along approximately about 35%, 45%, 55%, or 65% of the length $L_{54}$ of the cap member 54. Referring to FIG. 1, the first and second openings 78*a*, 78*b* may include an "L-shaped" geometry. As will be described in the following disclosure at FIGS. 5F-5G, the "L-shaped" geometry of the first and second openings 78*a*, 78*b* permits the cap member 54 to be interfacingly-locked with a pair of flanges 80 (see, e.g., FIG. 1) that are arranged proximate the distal end portion 20 of the tube-shaped body 16. As seen in FIG. 1, each flange 80*a*, 80*b* of the pair of flanges 80 extend radially outwardly from the outer surface 24 of the tube-shaped body 16 in a diametrically-opposing relationship.

In an example, the third opening 78*c* may be formed by the proximal end surface 66 of the cap member 54. In some implementations, the third opening 78*c* may be axially-aligned with the central axis, A-A; as a result, the third opening 78*c* may alternatively be referred to as an axial opening.

The first opening 78*a* and the second opening 78*b* permit the recess 76 of the cap member 54 to be in radial fluid communication with surrounding atmosphere, A. The third opening 78*c* permits the recess 76 of the cap member 54 to be in axial fluid communication with the surrounding atmosphere, A.

Referring to FIGS. 5A-5G, an exemplary method for operating the syringe-assist device 10 is described as follows. Firstly, as seen in FIGS. 5A-5D, the syringe-supporting member 34 is slidably-adjusted within the axial passage 28 from a lowered, at-rest orientation (as seen in, e.g., FIGS. 5A-5B) to a raised orientation (as seen in, e.g., FIG. 5C). Slidable adjustment of the syringe-supporting member 34 within the axial passage 28 may be result from the user U grasping the handle 42 and elevating the syringe-supporting member 34 with respect to the tube-shaped body 16.

Once the syringe-supporting member 34 is adjusted to the raised orientation as seen in FIG. 5C, the axial passage 28 may be further defined to include a first, proximal passage portion 28*a* and a second, distal passage portion 28*b*. As seen in FIG. 5C, the user U may then dispose the container C within the first, proximal passage portion 28*a* such that a lower, proximal end surface $C_p$ of the container C is disposed adjacent the proximal end portion 48 of the receiving pocket 48 of the base member 46. The user U may arrange the container C within the first, proximal passage portion 28*a* of the tube-shaped body 16 such that the fluid-flow passage 44 that extends through the thickness $T_{34}$ of the syringe-supporting member 34 is axially-aligned with an opening, $C_O$ formed by the upper, distal end surface $C_D$ of the container C in order to permit the fluid-flow passage 44 of the syringe-supporting member 34 to be in fluid communication with a filtered fluid reservoir $C_R$ (see, e.g., FIG. 6D) defined by the container C.

Referring to FIG. 5D, the user U may then slidably-adjust the syringe-supporting member 34 in a direction back toward the lowered, at-rest orientation such that the proximal end surface 36 of the syringe-supporting member 34 is disposed adjacent an upper, distal end surface, $C_D$ of the container C. Once the proximal end surface 36 of the syringe-supporting member 34 is disposed adjacent an upper, distal end surface $C_D$ of the container C, the syringe-supporting member 34 is supported by the container C within the tube-shaped body 16 and prevented from sliding further in a direction toward the lowered, at-rest orientation of FIG. 5A.

Once the proximal end surface 36 of syringe-supporting member 34 is disposed adjacent the upper, distal end surface $C_D$ of the container C as described above, the user U may then arrange the syringe S in the second, distal passage portion 28*b* of the axial passage 28. Once the syringe S is arranged in the axial passage 28, the user U may dispose a distal tip $F_D$ of the wheel filter F in the fluid-flow passage 44 of the syringe-supporting member 34 by inserting the distal tip $F_D$ of the wheel filter F into the second, distal opening 44*b* formed by the outer distal end surface 38 of the syringe-supporting member 34.

Once the syringe S and the container C are retained within the housing portion 12 of the syringe-assist device 10 as described above, the user U may then actuate the actuator portion 14. Referring to FIG. 5E, the user U may actuate the actuator portion 14 by firstly applying a pushing force Y to the cap member 54. The pushing force Y results in the cylinder 50*b* of the actuator 50 being advanced through the first opening 30*a* formed by the distal end portion 20 of the tube-shaped body 16, and, as a result, the piston rod 50*a* and the head member 52 are advanced through the first, proximal passage portion 28*a* of the axial passage 28 and toward the pushing head H of the plunger P of the syringe S (see, e.g., FIGS. 6A-6B).

Once the actuator portion 14 is advanced through the axial passage 28 of the tube-shaped body 16 of the housing portion 12 as described above, the proximal end surface 60 of the head member 52 of the actuator portion 14 directly engages the pushing head H of the plunger P of the syringe S. As the userU continues to apply the pushing force Y movement of the plunger P into the unfiltered fluid reservoir R (see, e.g., FIGS. 6A-6B) formed by the tube-shaped member T of the syringe S is impeded as a result of the unfiltered fluid UF being disposed within the unfiltered fluid reservoir R; therefore, the inclusion of the unfiltered fluid UF within the unfiltered fluid reservoir R causes plunger P of the syringe S to counteract the pushing force Y imparted by the user U which results in the piston rod 50*a* of the actuator 50 being urged into the cylinder 50*b* of the actuator 50 (as seen in FIG. 5F) as the user U continues to impart the pushing force Y to the cap member 54.

Transitioning from FIG. 5E to FIG. 5F, as the user U urges the cap member 54 toward the distal end portion 20 of the tube-shaped body 16 of the housing portion 12, the first and second flanges 80*a*, 80*b* enter a first branch of the "L-shaped" first and second openings 78*a*, 78*b* formed by the cap member 54. The user U may further urge the cap member 54 according to the direction of the arrow Y until the inner distal end surface 74 of the cap member 54 is disposed approximately adjacent the distal end portion 20 of the tube-shaped body 16.

Then, as seen in FIG. 5F, the user U may apply a second motion to the actuator portion 14 by twisting the end cap 54 according to the direction of the arrow Z. Referring to FIG. 5G, upon twisting the cap member 54 according to the direction of the arrow Z the first and second flanges 80*a*, 80*b* enter a second branch of the "L-shaped" first and second openings 78*a*, 78*b* that is substantially perpendicular to the first branch of the "L-shaped" first and second openings 78*a*, 78*b*. Once the first and second flanges 80*a*, 80*b* have entered the second branch of the "L-shaped" first and second openings 78*a*, 78*b*, the cap member 54 is arranged in a locked orientation with respect to the tube-shaped body 16 of the housing portion 12.

Once the cap member 54 is arranged in the locked orientation with respect to the tube-shaped body 16 of the housing portion 12, the gas that is contained within the cylinder 50*b* prevents the cylinder 50*b* from urging the cap member 54 away from the tube-shaped body 16 due to the fact that the first and second flanges 80*a*, 80*b* are disposed within the second branch of the "L-shaped" first and second openings 78*a*, 78*b* to thereby lock the cap member 54 to the tube-shaped body 16. Therefore, the gas that is contained within the cylinder 50*b* of the actuator 50 may urge the piston 50*a* away from and out of the cylinder 50*b* for returning the piston rod 50*a* back to the extended state. As the piston 50*a* is urged back to the extended state, the piston 50*a* imparts the plunger-actuating force X' to the pushing head H of the plunger P for evacuating the unfiltered fluid UF from the unfiltered fluid reservoir R and out of the proximal end Sp of the syringe S such that the unfiltered fluid UF may pass through the wheel filter F. Once the unfiltered fluid UF passes through the wheel filter F the unfiltered fluid UF may thereafter be referred to as filtered fluid FF. The filtered fluid FF may then exit the wheel filter F and be directed toward the fluid-flow passage 44 formed by the syringe-supporting member 34. The filtered fluid FF may then exit the fluid-flow passage 44 and enter the filtered fluid container C by way of the opening $C_O$ of the filtered fluid container C that is in fluid communication with the fluid-flow passage 44 formed by the syringe-supporting member 34.

The present invention has been described with reference to certain exemplary embodiments thereof. However, it will be readily apparent to those skilled in the art that it is possible to embody the invention in specific forms other than those of the exemplary embodiments described above. This may be done without departing from the spirit of the invention. The exemplary embodiments are merely illustrative and should not be considered restrictive in any way. The scope of the invention is defined by the appended claims and their equivalents, rather than by the preceding description.

What is claimed is:

1. A syringe-assist device, comprising:

a housing portion that defines an axial passage;

an actuator portion partially disposed within the axial passage of the housing portion, wherein the actuator portion includes:

an actuator member having a proximal end and a distal end, a head member connected to the proximal end of the actuator member, and a cap member connected to the distal end of the actuator member, wherein the cap member includes an outer side surface and an inner side surface, wherein the inner side surface defines the cap member to include an inner diameter that is slightly greater than a body diameter defined by an outer surface of the housing portion, wherein the cap member includes a first locking hole and a second locking hole; and a syringe-supporting member movably-disposed within the axial passage, wherein the syringe-supporting member fluidly separates the axial passage into a first passage portion and a second passage portion, wherein the actuator portion is movably-disposed within the second passage portion of the axial passage, wherein syringe-supporting member defines a fluid-flow passage that fluidly-connects the first passage portion of the axial passage to the second passage portion of the axial passage.

2. The syringe-assist device according to claim 1, wherein the housing portion is a tube-shaped body having a proximal end portion, a distal end portion and a side portion extending between the proximal end portion and the distal end portion, wherein each of the proximal end portion, the distal end portion and the side portion are defined by an outer surface and an inner surface such that the tube-shaped housing portion is defined by a thickness extending between the outer surface and the inner surface.

3. The syringe-assist device according to claim 2, wherein the inner surface defines the axial passage, wherein the axial passage extends through the tube-shaped housing portion along a central axis between the proximal end portion and the distal end portion of the tube-shaped housing portion, wherein the inner surface defines the axial passage to form an axial passage diameter, wherein the outer surface defines the tube-shaped housing portion to form a body diameter.

4. The syringe-assist device according to claim 2, wherein the tube-shaped housing portion forms a first opening and a second opening each extending through the thickness of the tube-shaped housing portion, wherein the first opening is formed in the distal end portion of the tube-shaped housing portion and is axially-aligned with the central axis, wherein the second opening is formed in the side portion of the tube-shaped body.

5. The syringe-assist device according to claim 4, wherein the second opening extends along a portion of a length of the tube-shaped body, wherein the second opening is approximately equal to but slightly greater than half of a circumference of the tube-shaped body.

6. The syringe-assist device according to claim 1, wherein the syringe-supporting member includes a handle extending from the syringe-supporting member.

7. The syringe-assist device according to claim 1, wherein the syringe-supporting member includes a diameter that is slightly less than an axial passage diameter formed by the axial passage of the tube-shaped housing portion.

8. The syringe-assist device according to claim 1, further comprising:

a base member connected to a proximal end portion of the housing portion.

9. The syringe-assist device according to claim 1, wherein a first portion of the actuator portion is movably-disposed within the second passage portion of the axial passage, wherein a second portion of the actuator portion is arranged exterior of the housing portion.

10. The syringe-assist device according to claim 1, wherein the actuator member includes a piston rod that is movably-disposed within a cylinder.

11. The syringe-assist device according to claim 10, wherein the piston rod contains a gas.

12. The syringe-assist device according to claim 1, wherein the head member includes a diameter that is slightly less than a diameter of the axial passage of the housing portion.

13. The syringe-assist device according to claim 1, wherein the first locking hole and the second locking hole are arranged in a diametrically-opposing relationship.

14. The syringe-assist device according to claim 1, wherein each of the first locking hole and the second locking hole include an L-shaped geometry.

15. The syringe-assist device according to claim 14, further comprising:

a first flange and a second flange located at a distal end portion of the housing , wherein when the cap member is selectively-arranged upon the distal end portion of the housing such that the first flange and the second flange are respectively-arranged within the first locking hole and the second locking hole the cap member is selectively-coupled to the distal end portion of the housing.

16. A method, comprising the steps of:

providing a syringe-assist device according to claim 1;

removably-disposing a container within the first passage portion of the axial passage such that the container is in fluid communication with a proximal opening of the fluid-flow passage;

removably-disposing a syringe within the second passage portion of the axial passage such that the syringe is in fluid communication with a distal opening of the fluid-flow passage; and actuating the actuator portion for discharging a fluid contained within the syringe through the fluid-flow passage and into the container.

17. The method according to claim 16, wherein the removably-disposing the container step includes:

arranging a lower end surface of the container adjacent a proximal end portion of the tube-shaped housing portion; and arranging a proximal end surface of the syringe-supporting member adjacent an upper end surface of the container.

18. The method according to claim 16, wherein the removably-disposing the syringe step includes:

disposing a distal tip of a wheel filter attached to a proximal end of the syringe in the fluid-flow passage of the syringe-supporting member.

19. The method according to claim 16, wherein the actuating the actuator portion step includes:

applying a pushing force to the distal end of the actuator portion.

20. The method according to claim 19, wherein the actuator member includes a piston rod movably-disposed within a cylinder and wherein the applied pushing force results in the piston rod engaging with a plunger of the syringe and the piston rod retracting into the cylinder.

21. The method according to claim 19, further comprising the steps of:

twisting the distal end of the actuator portion for locking the distal end of the actuator portion to a distal end portion of the housing portion.

22. The method according to claim 21, further comprising the steps of:

extending the piston rod from the cylinder and toward the plunger of the syringe for discharging the fluid contained within the syringe through the fluid-flow passage and into the container.

* * * * *